(12) United States Patent
Maruyama et al.

(10) Patent No.: US 9,513,305 B2
(45) Date of Patent: Dec. 6, 2016

(54) MULTIPLE CLEANING STATIONS FOR A DISPENSING PROBE

(71) Applicant: Toshiba Medical Systems Corporation, Otawara-shi (JP)

(72) Inventors: Reiko Maruyama, Nasushiobara (JP); Shoichi Kanayama, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 53 days.

(21) Appl. No.: 14/197,705

(22) Filed: Mar. 5, 2014

(65) Prior Publication Data

US 2014/0186234 A1 Jul. 3, 2014

Related U.S. Application Data

(63) Continuation of application No. PCT/JP2013/073997, filed on Sep. 5, 2013.

(30) Foreign Application Priority Data

Sep. 11, 2012 (JP) .................................. 2012-199810

(51) Int. Cl.
  *G01N 35/10* (2006.01)
(52) U.S. Cl.
  CPC ................... *G01N 35/1004* (2013.01)
(58) Field of Classification Search
  CPC ............................................. G01N 35/1004
  See application file for complete search history.

(56) References Cited

U.S. PATENT DOCUMENTS

2011/0274584 A1* 11/2011 Kitamura et al. .............. 422/63
2011/0293474 A1* 12/2011 Sugimura et al. .............. 422/62
(Continued)

FOREIGN PATENT DOCUMENTS

| CN | 102288773 A | 12/2011 |
|---|---|---|
| JP | 01-209372 | 8/1989 |

(Continued)

OTHER PUBLICATIONS

English translation of the International Search Report issued Oct. 15, 2013, in PCT/JP2013/073997.

(Continued)

*Primary Examiner* — Jill Warden
*Assistant Examiner* — Benjamin Whatley
(74) *Attorney, Agent, or Firm* — Oblon, McClelland, Maier & Neustadt, L.L.P.

(57) ABSTRACT

An automatic analysis apparatus according to an embodiment incudes a dispensing probe, a cleaning unit, and a driving mechanism. The dispensing probe performs a dispensing operation for sucking a sample and discharging the sample into a reaction container. The cleaning unit cleans the dispensing probe. The cleaning unit includes a first cleaning position at which the dispensing probe is cleanable using a first cleaning liquid, and a second cleaning position which is located at a position lower than the first cleaning position and at which the dispensing probe is cleanable using a second cleaning liquid. The driving mechanism stops the dispensing probe at at least one of the first cleaning position and the second cleaning position.

10 Claims, 10 Drawing Sheets

(56) References Cited

U.S. PATENT DOCUMENTS

2014/0037503 A1\* 2/2014 Sakashita ........... G01N 35/1004
422/81
2015/0192601 A1\* 7/2015 Cohen ................... G01N 35/10

FOREIGN PATENT DOCUMENTS

| | | | | |
|---|---|---|---|---|
| JP | 10-267939 A | 10/1998 | | |
| JP | 10-267939 A | \* 10/1998 | ............ | G01N 35/00 |
| JP | 2945747 B2 | 9/1999 | | |
| JP | 2000-046844 | 2/2000 | | |
| JP | 2010-060522 | 3/2010 | | |
| JP | 2011-257386 A | 12/2011 | | |
| JP | WO 2012105398 A1 \* | 8/2012 | ......... | G01N 35/1004 |

OTHER PUBLICATIONS

Chinese Office Action issued Sep. 30, 2014, in China Patent Application No. 201380001582.9 (with English translation).
International Search Report issued on Oct. 15, 2013 for PCT/JP2013/073997 filed on Sep. 5, 2013 with English Translation of Categories of Cited Documents.
International Written Opinion issued on Oct. 15, 2013 for PCT/JP2013/073997 filed on Sep. 5, 2013.

\* cited by examiner

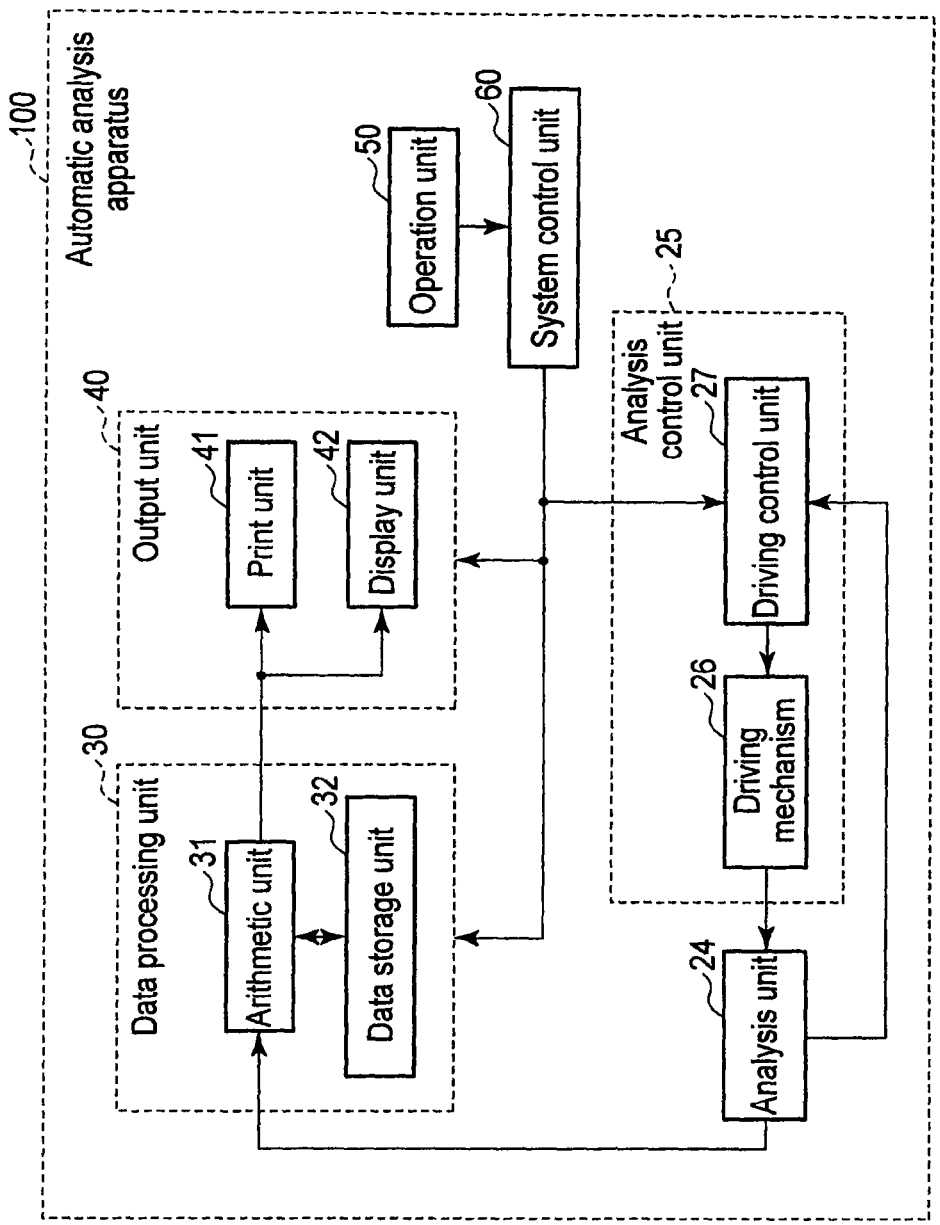
F I G. 1

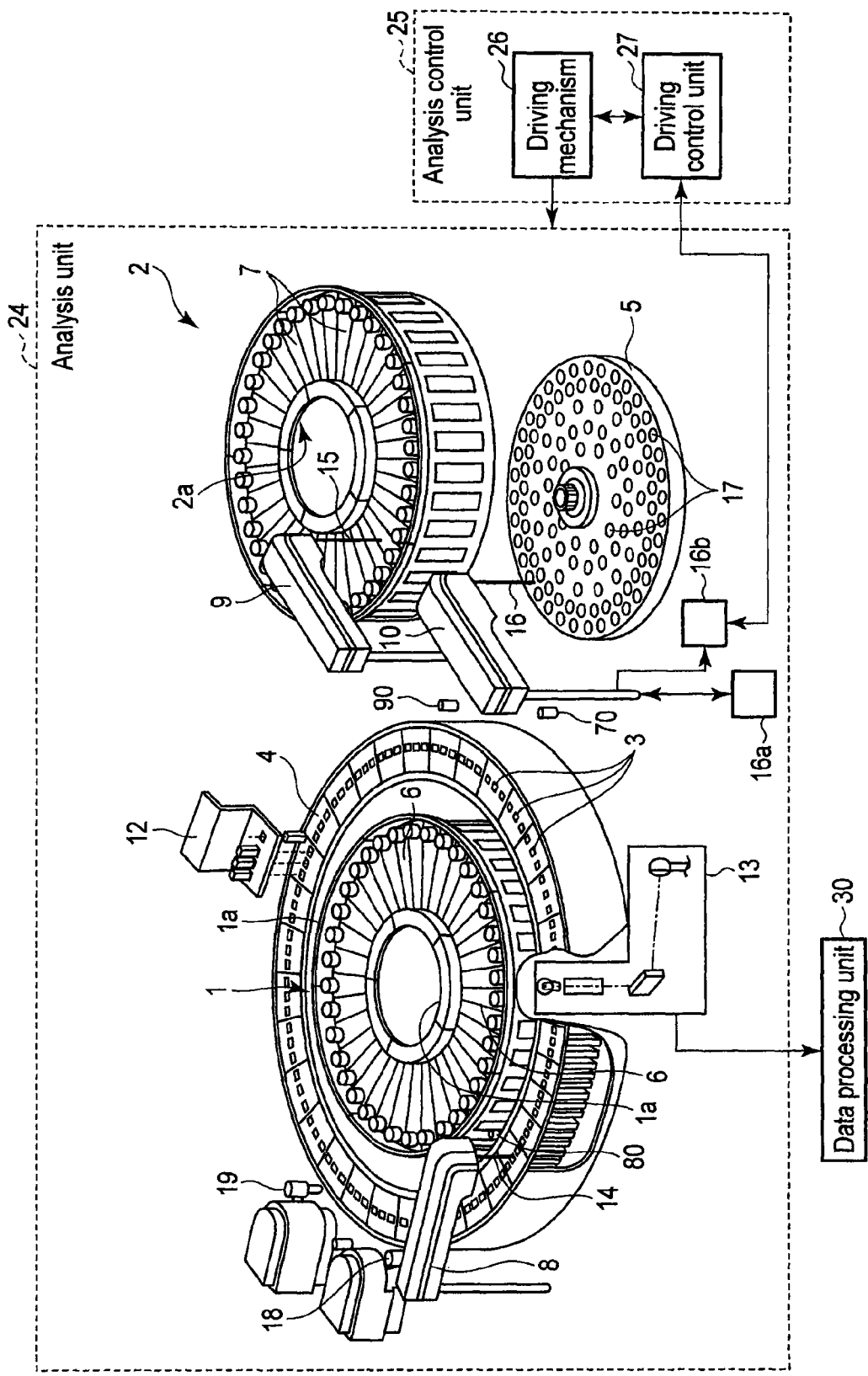
F I G. 2

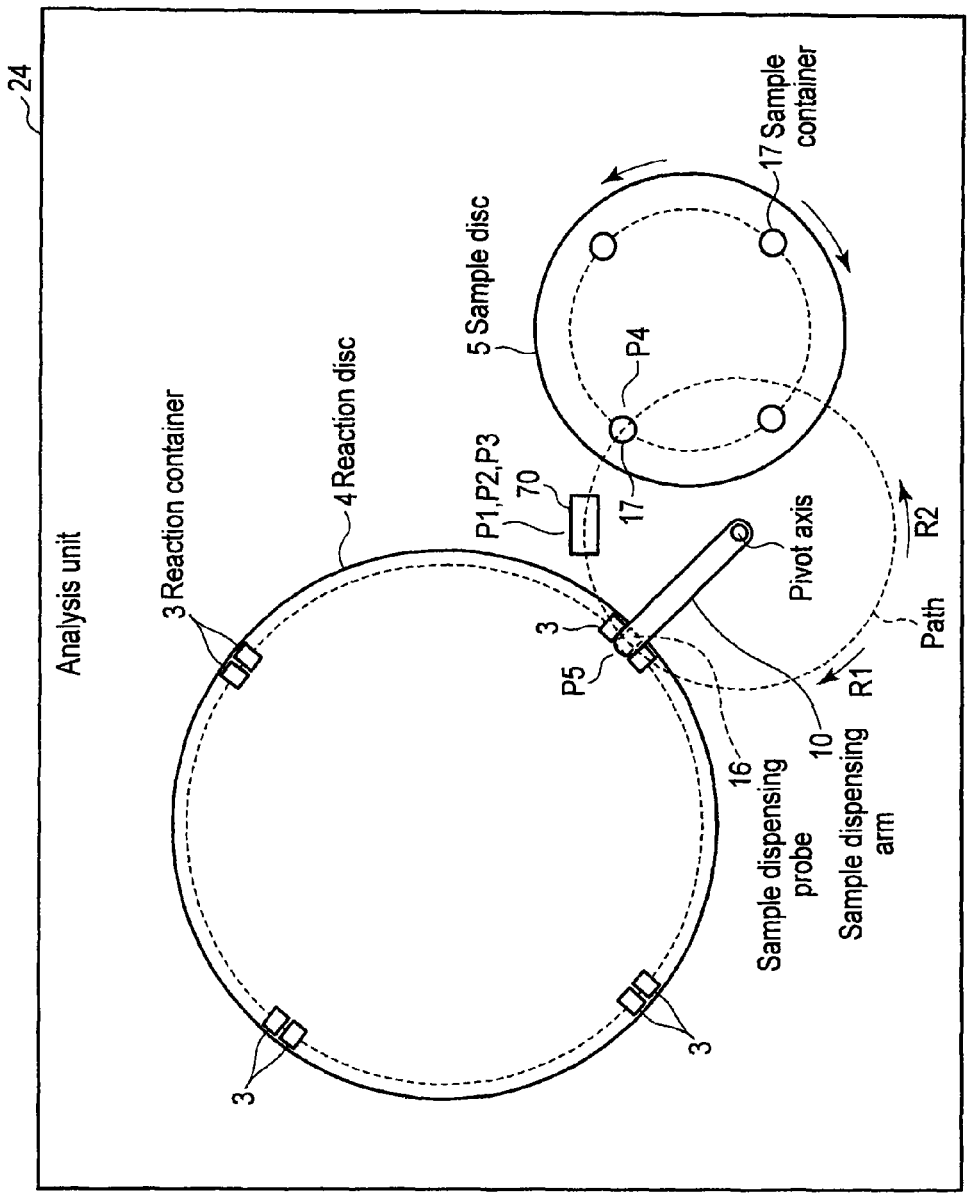
F I G. 4

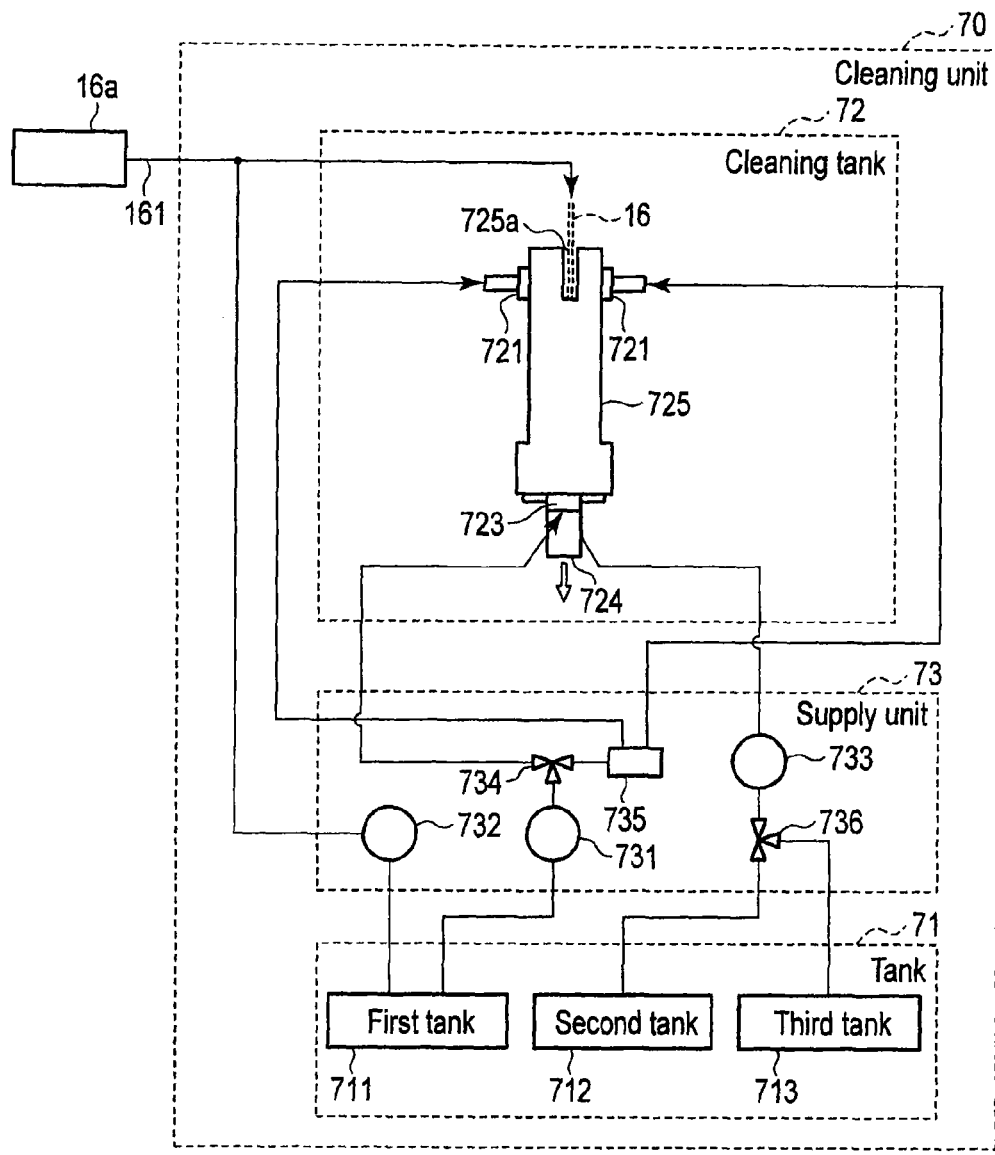
F I G. 5

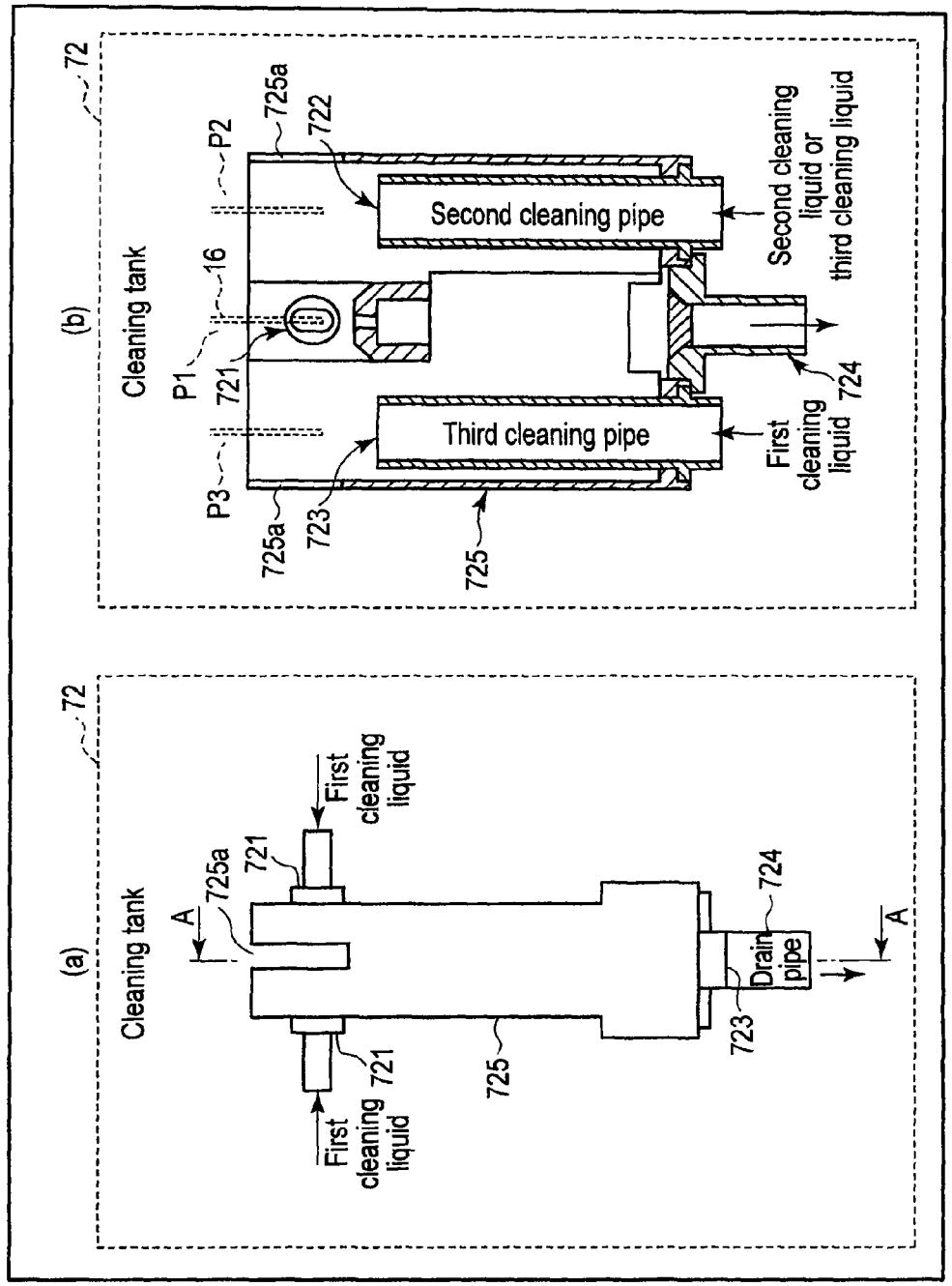
F I G. 6

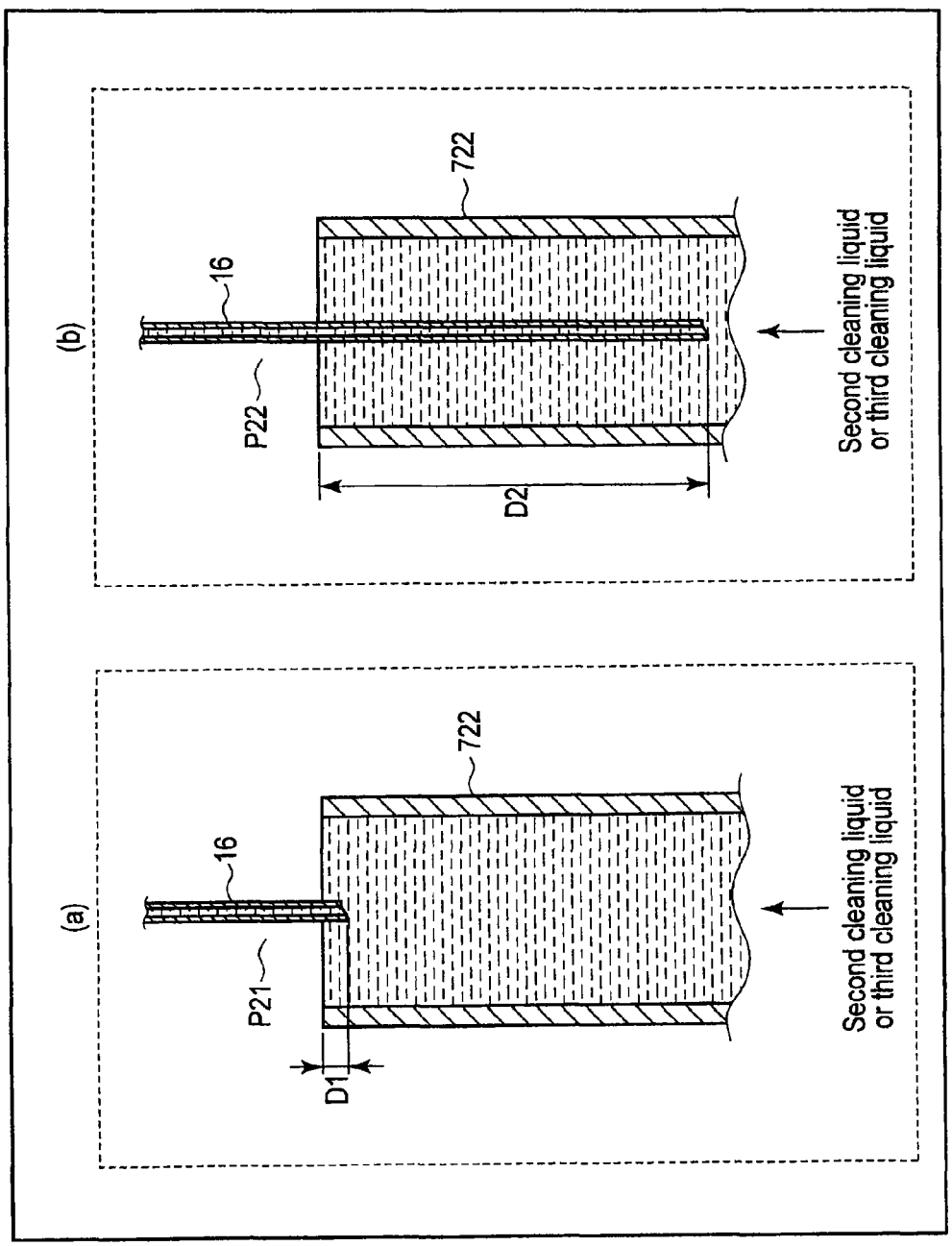
F I G. 8

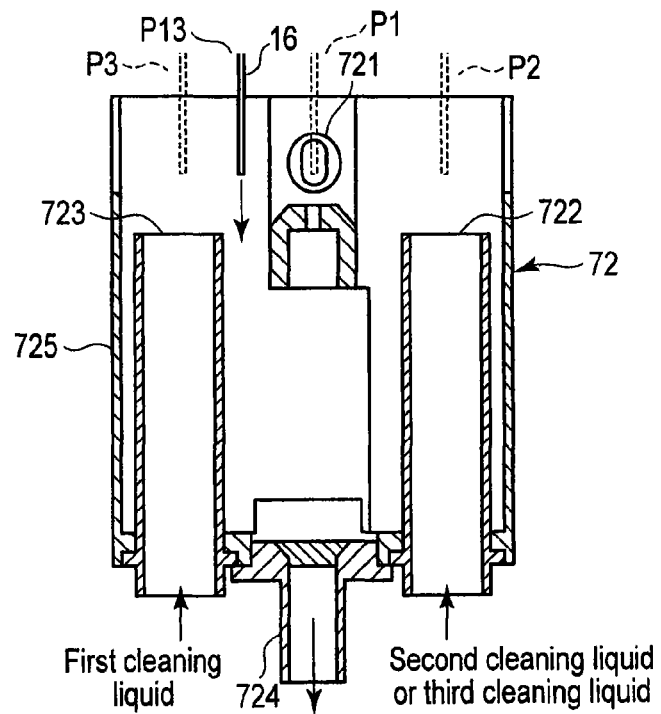
F I G. 9
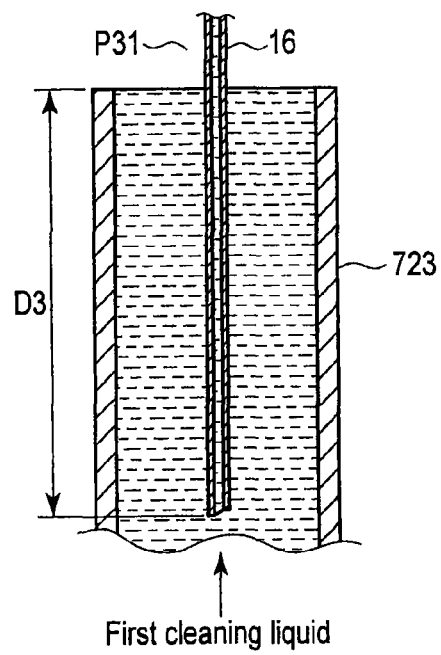
F I G. 10

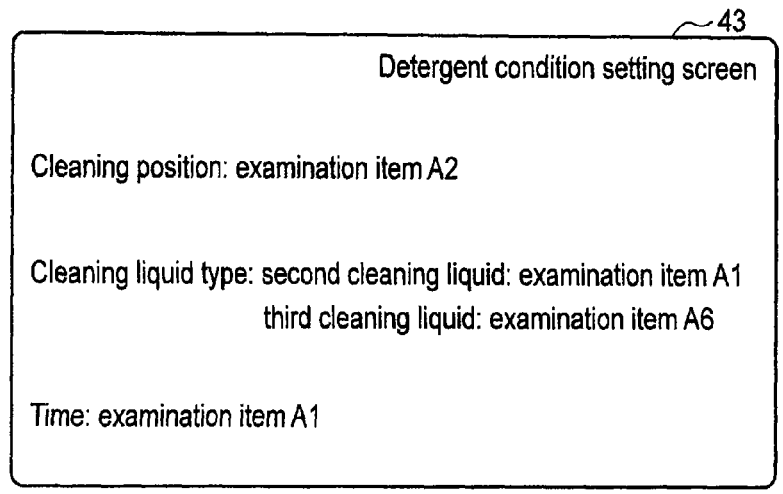

FIG. 11

| Sample to be examined | Set examination item | Cleaning condition | | |
|---|---|---|---|---|
| | | Cleaning position | Cleaning liquid | Cleaning time |
| B1 | A1 → A2 | Third cleaning position | First cleaning liquid | T0 |
| B2 | A2 | Second cleaning position | Second cleaning liquid | T1 |
| B3 | A1 | First cleaning position | Second cleaning liquid | T1 |
| B4 | A1 → A2 | Third cleaning position | First cleaning liquid | T0 |
| B5 | A3 → A4 | First cleaning position | First cleaning liquid | T0 |

FIG. 12

MULTIPLE CLEANING STATIONS FOR A DISPENSING PROBE

CROSS-REFERENCE TO RELATED APPLICATIONS

This application is a Continuation Application of PCT Application No. PCT/JP2013/073997, filed Sep. 5, 2013 and based upon and claims the benefit of priority from the Japanese Patent Application No. 2012-199810, filed Sep. 11, 2012, the entire contents of all of which are incorporated herein by reference.

FIELD

Embodiments described herein relate generally to an automatic analysis apparatus including a function of cleaning a dispensing probe which dispenses a sample.

BACKGROUND

According to aspects of one embodiment, there is provided an automatic analysis apparatus targets at biochemical examination items, immunological examination items, and the like. The automatic analysis apparatus optically measures changes in absorbance and turbidity caused by reactions in a mixed liquid between a sample such as a sample to be examined obtained from a subject and a reagent of each examination item using a photometry unit. Then, the automatic analysis apparatus generates analysis data expressed by the concentrations of examination item components, enzyme activity, and the like in a sample.

For each sample to be examined, this automatic analysis apparatus analyzes a set of examination items from a plurality of examination items. Then, a sample dispensing probe sucks each sample to be examined contained in a sample container, and discharges it into a reaction container. Also, a reagent dispensing probe sucks a reagent contained in a reagent container, and discharges it into the reaction container. The photometry unit measures the absorbance and turbidity of a mixed liquid of the sample to be examined and reagent discharged into the reaction container. Then, the sample dispensing probe is cleaned at every sample dispensing end timing. Also, the reagent dispensing probe is cleaned at every reagent dispensing end timing.

As the sample container used by the automatic analysis apparatus, a blood collection tube which contains whole blood collected from a subject is known. The whole blood contained in the blood collection tube is often separated by a centrifugal separator into an upper layer sample containing a blood serum or plasma, and a lower layer sample containing blood cell components and the like. The automatic analysis apparatus dispenses the upper layer sample and lower layer sample to analyze respective examination items. Then, the examination items include an item which requires high-sensitive analysis using the upper layer sample.

However, when the upper layer sample is sucked after the lower layer sample is dispensed, and when the examination item which requires high-sensitive analysis is set for a sample to be examined, analysis data of the examination item set for the sample to be examined is deteriorated by contamination of the sample attached to an outer wall of the sample dispensing probe, thus posing a problem.

BRIEF DESCRIPTION OF THE DRAWINGS

FIG. 1 is a block diagram showing the arrangement of an automatic analysis apparatus according to an embodiment.

FIG. 2 is a perspective view showing the arrangement of an analysis unit according to the embodiment.

FIG. 4 is a view showing respective positions at which the sample dispensing probe according to the embodiment is stopped.

FIG. 5 is a view showing an example of the arrangement of a cleaning unit according to the embodiment.

FIG. 6 is a view showing the arrangement of a cleaning tank according to the embodiment.

FIG. 8 is a view showing the sample dispensing probe stopped at first and second cleaning positions according to the embodiment.

FIG. 9 is a view showing the sample dispensing probe stopped at a special inner wall cleaning position according to the embodiment.

FIG. 10 is a view showing the sample dispensing probe stopped at a third cleaning position according to the embodiment.

FIG. 11 is a view showing an example of a special cleaning condition setting screen displayed on a display unit according to the embodiment.

FIG. 12 is a table showing an example of a plurality of samples to be examined, and examination items and cleaning conditions set for respective samples to be examined according to the embodiment.

DETAILED DESCRIPTION

Figure 3:
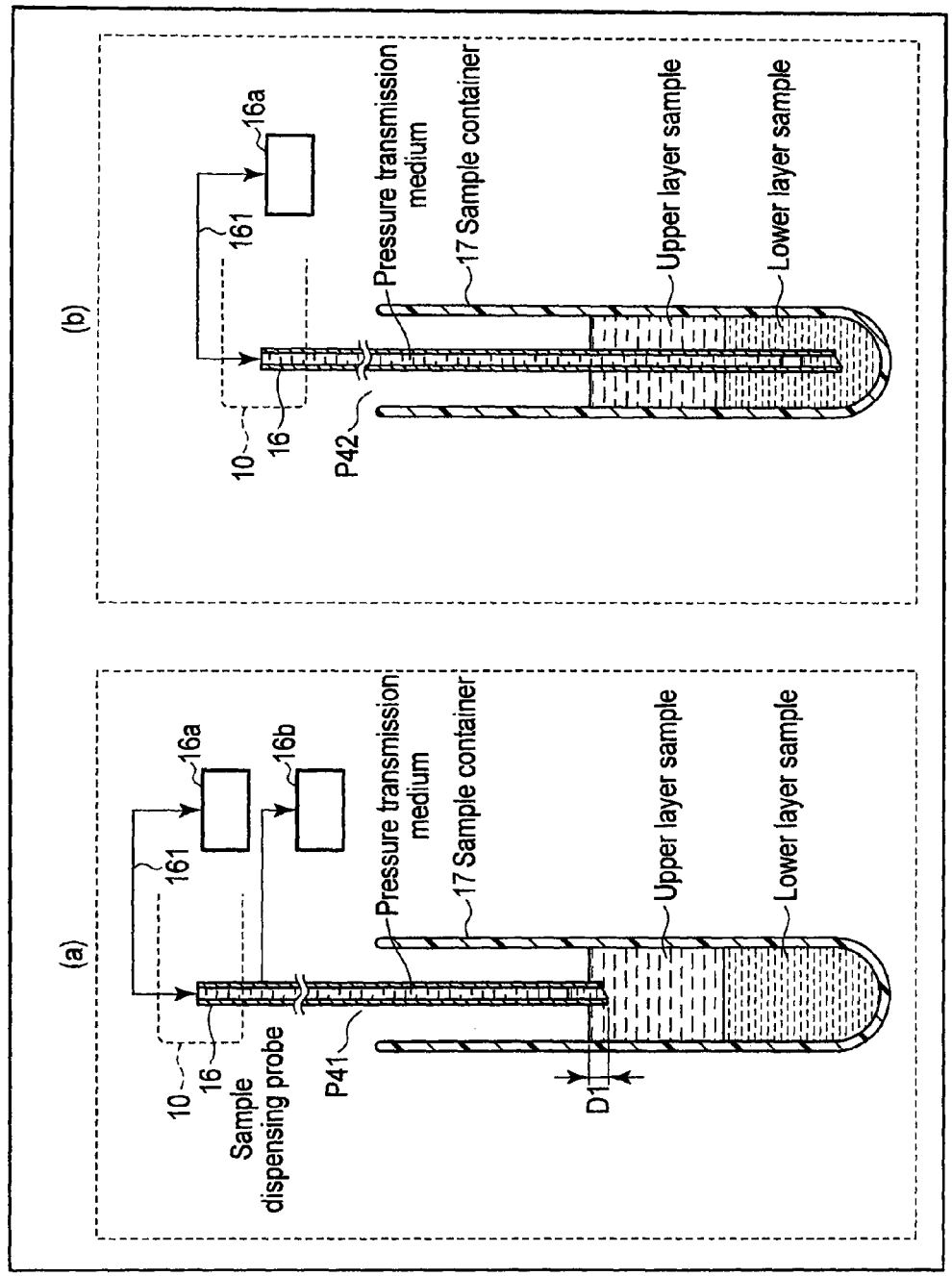
FIG. 3 is a view showing a sample dispensing probe, sample dispensing arm, sample dispensing pump, liquid level detector, and sample container, which are used to dispense a sample to be examined according to the embodiment.

An automatic analysis apparatus according to an embodiment includes a dispensing probe, a cleaning unit, and a driving mechanism.

The dispensing probe performs a dispensing operation for sucking a sample and discharging the sample into a reaction container.

The cleaning unit cleans the dispensing probe. The cleaning unit includes a first cleaning position at which the dispensing probe is cleanable using a first cleaning liquid, and a second cleaning position which is located at a position lower than the first cleaning position and at which the dispensing probe is cleanable using a second cleaning liquid.

The driving mechanism stops the dispensing probe at at least one of the first cleaning position and the second cleaning position.

An embodiment will be described hereinafter with reference to the drawings.

FIG. 1 is a block diagram showing the arrangement of an automatic analysis apparatus according to an embodiment.

This automatic analysis apparatus 100 includes an analysis unit 24, which dispenses a sample such as a standard sample or sample to be examined of each examination item, and a reagent used in analysis of each examination item, and measures a mixed liquid of the sample and reagent to generate standard data and examined data, and an analysis control unit 25 which drives respective units of the analysis unit 24 to control a dispensing operation, measuring operation, cleaning operation, and the like.

Also, the automatic analysis apparatus 100 includes a data processing unit 30 which processes the standard data and examined data generated by the analysis unit 24 to generate calibration data and analysis data, an output unit 40 which prints or displays the calibration data and analysis data generated by the data processing unit 30, an operation unit 50 which is used to input various command signals and the like, and a system control unit 60 which systematically controls the analysis control unit 25, data processing unit 30, and output unit 40.

FIG. 2 is a perspective view showing the arrangement of the analysis unit 24. This analysis unit 24 includes sample containers 17 which contain standard samples, respective samples to be examined such as urine, whole blood, a sample separated into upper and lower layers from whole blood by centrifugal separation, and a sample of the separated upper layer, and the like, and a sample disc 5 which holds the sample containers 17. Also, the analysis unit 24 includes reagent containers 6 which contain first reagents of one- and two-reagent types, which react with components of examination items contained in respective samples such as standard samples and samples to be examined, a reagent rack 1a which pivotally holds the reagent containers 6, and a reagent storage 1 which stores the reagent containers 6 held in the reagent rack 1a cold.

The analysis unit 24 includes reagent containers 7 which contain second reagents paired with the first reagents of the two-reagent type, a reagent rack 2a which pivotally holds the reagent containers 7, a reagent storage 2 which stores the reagent containers 7 held in the reagent rack 2a cold, and a reaction disc 4 which rotatably holds a plurality of reaction containers 3 arranged on the circumference.

Furthermore, the analysis unit 24 includes a sample dispensing probe 16 which performs a dispensing operation for sucking each sample in the sample container 17 held in the sample disc 5 and discharging it into a reaction container 3, a sample dispensing pump 16a which controls the sample dispensing probe 16 to suck and discharge a sample, and a sample dispensing arm 10 which pivotally and vertically movably holds the sample dispensing probe 16. Moreover, the analysis unit 24 includes a cleaning unit 70 which cleans the sample dispensing probe 16 at every sample dispensing end timing, and a liquid level detector 16b which detects a sample in each sample container 17 held in the sample disc 5 by a contact between this sample and the sample dispensing probe 16.

In addition, the analysis unit 24 includes a first reagent dispensing probe 14 which performs a dispensing operation for sucking a first reagent in each reagent container 6 held in the reagent rack 1a, and discharging it into the reaction container 3 in which a sample is discharged, a first reagent dispensing arm 8 which pivotally and vertically movably holds the first reagent dispensing probe 14, a cleaning unit 80 which cleans the first reagent dispensing probe 14, and a first stirrer 18 which stirs a mixed liquid of the sample and first reagent discharged in the reaction container 3.

Also, the analysis unit 24 includes, in the reaction container 3 where the first reagent has been discharged, a second reagent dispensing probe 15 which performs a dispensing operation for sucking a second reagent in each reagent container 7 held in the reagent rack 2a and discharging it. The analysis unit 24 includes a second reagent dispensing arm 9 which pivotally and vertically movably holds this second reagent dispensing probe 15, a cleaning unit 90 which cleans the second reagent dispensing probe 15, and a second stirrer 19 which stirs a mixed liquid of the sample and the first and second reagent in the reaction container 3. The analysis unit 24 further includes a photometry unit 13 which performs optical measurement by irradiating a mixed liquid in the reaction container 3 with light, and a reaction container cleaning unit 12 which cleans the interior of the reaction container 3 which has been measured by the photometry unit 13.

Then, the photometry unit 13 irradiates the reaction container 3 with light, and detects light transmitted through a mixed liquid containing a standard sample or each sample to be examined in the reaction container 3. Then, the photometry unit 13 generates standard data and examined data used to calculate, for example, absorbance based on the detected detection signal, and outputs the generated standard data and examined data to the data processing unit 30.

The analysis control unit 25 includes a driving mechanism 26 which drives the respective units of the analysis unit 24, and a driving control unit 27 which controls this driving mechanism 26. Then, the driving mechanism 26 executes pivot driving of the sample disc 5, and reagent racks 1a and 2a. Also, the driving mechanism 26 executes rotation driving of the reaction disc 4. The driving mechanism 26 executes pivot/vertical driving of the sample dispensing arm 10, and the first and second reagent dispensing arms 8 and 9 to move the sample dispensing probe 16, and the first and second reagent dispensing probes 14 and 15. Also, the driving mechanism 26 executes vertical driving of the reaction container cleaning unit 12. Furthermore, the driving mechanism 26 executes suction/discharge driving of the sample dispensing pump 16a. Moreover, the driving mechanism 26 executes cleaning driving of the cleaning units 70, 80, and 90. In addition, the driving mechanism 26 executes pivot/vertical driving of the stirrers 18 and 19.

The data processing unit 30 shown in FIG. 1 includes an arithmetic unit 31 which processes the standard data and examined data output from the photometry unit 13 of the analysis unit 24 to generate calibration data and analysis data of respective examination items, and a data storage unit 32 which stores the standard data and analysis data generated by the arithmetic unit 31.

The arithmetic unit 31 generates, based on standard data output from the photometry unit 13 and a standard value set in advance for a standard sample of this standard data, calibration data which represents a relationship between the standard value and standard data for each examination item. The arithmetic unit 31 outputs the generated calibration data to the output unit 40 and data storage unit 32. The data storage unit 32 stores the calibration data.

Also, the arithmetic unit 31 reads out, from the data storage unit 32, calibration data of an examination item corresponding to examined data output from the photometry unit 13. Then, the arithmetic unit 31 generates analysis data expressed by a concentration value or activity value from the examined data output from the photometry unit 13 using the readout calibration data. Then, the arithmetic unit 31 outputs the generated analysis data to the output unit 40, and stores that data in the data storage unit 32.

The data storage unit 32 includes a memory device such as a hard disk. The data storage unit 32 stores calibration data output from the arithmetic unit 31 for respective examination items. Also, the data storage unit 32 stores analysis data of respective examination items output from the arithmetic unit 31 for respective samples to be examined.

The output unit 40 includes a print unit 41, which prints calibration data and analysis data output from the arithmetic unit 31 of the data processing unit 30, and a display unit 42 which displays these data. Then, the print unit 41 includes a printer and the like. The print unit 41 prints calibration data and analysis data output from the arithmetic unit 31 on a print sheet or the like according to a pre-set format.

The display unit 42 includes a monitor such as a CRT (Cathode-Ray Tube) or liquid crystal panel. The display unit 42 displays calibration data and analysis data output from the arithmetic unit 31. Also, the display unit 42 displays an analysis parameter setting screen which allows the user to set analysis parameters (for example, a sample amount and reagent amount to be discharged in each reaction container 3, a suction position of a sample in each sample container 17, and the like) of examination items which can be analyzed by the automatic analysis apparatus 100. Furthermore, the display unit 42 displays a special cleaning condition setting screen which allows the user to set examination items for washing the sample dispensing probe 16 under a special cleaning condition different from a normal cleaning condition. Moreover, the display unit 42 displays an examination item setting screen which allows the user to set examination items of a subject to be examined for respective samples to be examined.

The operation unit 50 includes input devices including a keyboard, mouse, buttons, touch key panel, and the like. The operation unit 50 allows the user to make inputs required to set analysis parameters on the analysis parameter setting screen displayed on the display unit 42. The operation unit 50 allows the user to make inputs required to set examination items on the special cleaning condition setting screen displayed on the display unit 42. The operation unit 50 allows the user to make inputs required to set examination items for each sample to be examined on the examination item setting screen displayed on the display unit 42.

The system control unit 60 includes a CPU and storage circuit. The system control unit 60 controls the overall system by systematically controlling the analysis control unit 25, data processing unit 30, and output unit 40 based on the analysis parameters, examination items, and the like set by inputs from the operation unit 50.

The sample dispensing operation in the analysis unit 24 will be described below with reference to FIGS. 2, 3, and 4.

FIG. 3 shows the sample dispensing probe 16, sample dispensing arm 10, sample dispensing pump 16a, liquid level detector 16b, and sample container 17 used in the sample dispensing operation. This sample dispensing probe 16 is configured by a vertically elongated tube. An upper end portion of the sample dispensing probe 16 is held by the sample dispensing arm 10. An upper end of the tube of the sample dispensing probe 16 is connected to the sample dispensing pump 16a via a tube 161 filled up with a pressure transmission medium (for example, pure water or the like). Also, the sample dispensing probe 16 is electrically connected to the liquid level detector 16b.

The sample container 17 is, for example, a blood collection tube. The blood collection tube contains an upper layer sample containing a blood serum, and a lower layer sample containing red blood cells, white blood cells, and blood platelets. The upper layer sample is obtained by separating, for example, whole blood as a sample to be examined obtained from a subject by a centrifugal separator. The lower layer sample is obtained by separating whole blood by the centrifugal separator. That is, whole blood contained in the blood collection tube is centrifugally separated by the centrifugal separator to be separated into the upper layer sample and lower layer sample. In this manner, when the blood collection tube is used as the sample container 17, the efforts of transferring a sample from the blood collection tube to another container can be saved.

The liquid level detector 16b includes, for example, a capacitance sensor. The liquid level detector 16b detects the upper layer sample in the sample container 17 from a change in capacitance due to a contact between this sample and the sample dispensing probe 16. Then, the liquid level detector 16b outputs the detected detection signal to the driving control unit 27 of the analysis control unit 25.

The driving mechanism 26 executes pivot driving of the sample dispensing arm 10 at a level of an upper dead point. The driving mechanism 26 moves the sample dispensing probe 16 in a direction of an arrow R1 and in a direction of an arrow R2 opposite to the R1 direction on a circular path indicated by the broken line, as shown in FIG. 4. Then, the driving mechanism 26 stops the sample dispensing probe 16 at a normal cleaning position (first cleaning position) P1, special cleaning upper stop position P2, and special cleaning upper stop position P3. The normal cleaning position P1 is located on the path where the sample dispensing probe 16 can be cleaned by the cleaning unit 70 under a normal cleaning condition. The special cleaning upper stop position P2 is a position required to move the sample dispensing probe 16 located on one side in the vicinity of the normal cleaning position P1 on the path to a special cleaning position (second cleaning position) where cleaning is executed under a special cleaning condition. The special cleaning upper stop position P3 is a position required to move the sample dispensing probe 16 located on the other side in the vicinity of the normal cleaning position P1 on the path to a special cleaning position. Also, the driving mechanism 26 stops the sample dispensing probe 16 at a sample position P4 located above the sample container 17 held in the sample disc 5 on the path. Furthermore, the driving mechanism 26 stops the sample dispensing probe 16 at a reaction position P5 located above the reaction container 3 on the path.

By setting the normal cleaning position P1 on the path of the sample dispensing probe 16 in this way, the sample dispensing probe 16 at the reaction position P5, which ends the dispensing operation of each sample, can be quickly moved to the normal cleaning position P1.

The driving mechanism 26 drives the sample dispensing arm 10 downward based on information of a suction position included in analysis parameters of each examination item. Then, the driving mechanism 26 moves the sample dispensing probe 16 from the sample position P4 downward, and stops it at a position where its lower end portion enters the sample in the sample container 17.

Then, as shown in FIG. 3(a), the driving mechanism 26 stops the sample dispensing probe 16 at a normal suction position (first suction position) P41 lower by a first distance D1 than the contact position with the upper layer sample in the sample container 17. Then, the sample dispensing probe 16 sucks the upper layer sample by suction driving of the sample dispensing pump 16a.

By stopping the sample dispensing probe 16 at the normal suction position P41 in this way, contamination of a sample by the outer wall of the sample dispensing probe 16 can be suppressed by preventing a portion which is not required for suction of the outer wall of the sample dispensing probe 16 other than the first distance D1 from contacting the sample.

Also, as shown in FIG. 3(b), the driving mechanism 26 stops the sample dispensing probe 16 at a special suction position (second suction position) P42 at a lower position than the normal suction position P41, that is, a position lower by a second distance than the sample position P4 (upper surface of the sample container). Then, the sample dispensing probe 16 sucks the lower layer sample by suction driving of the sample dispensing pump 16a.

In this manner, in a suction operation for an examination item to be analyzed using the lower layer sample which is located in the lower layer of the samples separated into the upper and lower layers in the sample container 17, the driving mechanism 26 can stop the sample dispensing probe 16 at the special suction position P42 where it can suck the lower layer sample.

The arrangement of the cleaning unit 70 and a cleaning operation of the sample dispensing probe 16 will be described below with reference to FIGS. 2, 3, 4, 5, 6, and 7.

FIG. 5 is a view showing an example of the arrangement of the cleaning unit 70. This cleaning unit 70 includes a tank 71 which stores first to third cleaning liquids required to clean the sample dispensing probe 16, a cleaning tank 72 in which the sample dispensing probe 16 is cleaned using the first to third cleaning liquids stored in the tank 71, and a supply unit 73 which supplies the first to third cleaning liquids stored in the tank 71 to the cleaning tank 72 and sample dispensing probe 16.

The tank 71 includes a first tank 711 which stores the first cleaning liquid, a second tank 712 which stores the second cleaning liquid, and a third tank 713 which stores the third cleaning liquid. Then, the first tank 711 stores the first cleaning liquid (for example, pure water or the like) used in normal cleaning of the sample dispensing probe 16. The second tank 712 stores the second cleaning solution (for example, an alkaline cleaning liquid) which is used when cleaning is insufficient by the first and third cleaning liquids and when a detergency higher than the first and third cleaning liquids is to be obtained. The third tank 713 stores the third cleaning solution (for example, an acidic cleaning liquid) which is used when cleaning is insufficient by the first and second cleaning liquids and when a detergency higher than the first and second cleaning liquids is to be obtained.

FIG. 6 is a view showing the arrangement of the cleaning tank 72. FIG. 6(*a*) is a side view of the cleaning tank 72. FIG. 6(*b*) is a sectional view when an A-A section of the cleaning tank 72 shown in FIG. 6(*a*) is viewed from a direction parallel to the section. This cleaning tank 72 is configured by two first cleaning pipes 721 required to clean the outer wall of the sample dispensing probe 16 using the first cleaning liquid, and a second cleaning pipe 722 required to clean the outer wall and inner wall of the sample dispensing probe 16 using the second or third cleaning liquid.

Also, the cleaning tank 72 is configured by a third cleaning pipe 723 required to clean the sample dispensing probe 16 using the first cleaning liquid, a drain pipe 724 used to drain the first to third cleaning liquids used in cleaning, and a cleaning tank main body 725 which supports the first to third cleaning pipes 721 to 723 and the drain pipe 724.

Figure 7:
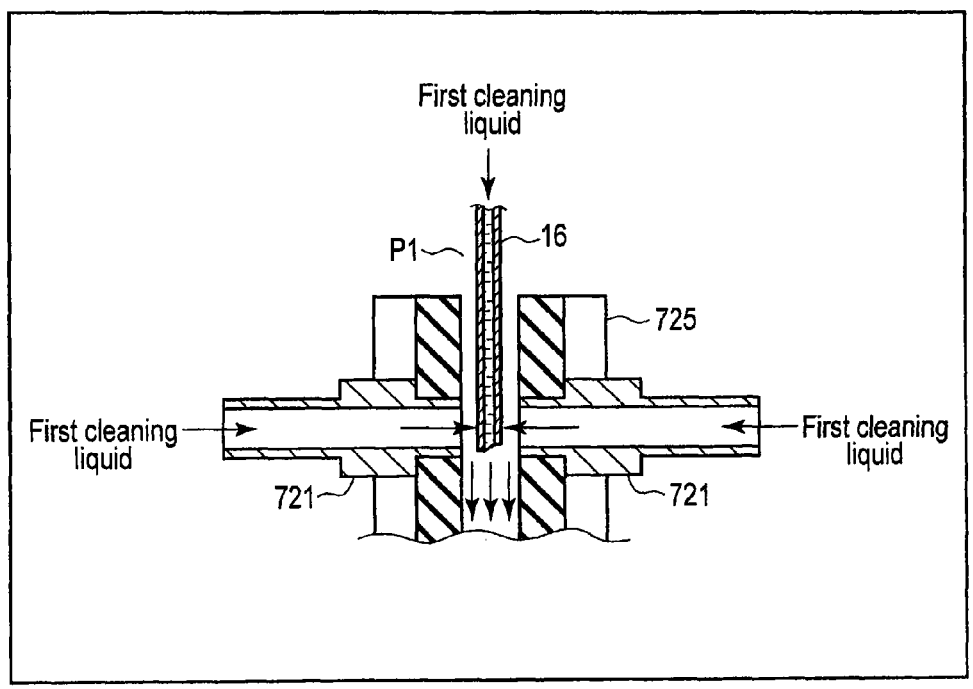
FIG. 7 is a view showing the sample dispensing probe stopped at a normal cleaning position according to the embodiment.

The first cleaning pipes 721 are disposed to oppose each other from, for example, a horizontal direction in the vicinity of an upper end portion of the cleaning tank main body 725, as shown in FIG. 7. For example, the first cleaning pipes 721 can be arranged with outlets that are diametrically opposed, such that the first outlet is arranged diametrically opposed to the second outlet. Further, the stream of the first cleaning liquid issuing from the first outlet can be counterposed to a stream of the first cleaning liquid issuing from the second outlet. Then, the first cleaning pipes 721 discharge the first cleaning liquid supplied from the supply unit 73 toward the sample dispensing probe 16 stopped at the normal cleaning position P1 from the two sides. With this discharging, the first cleaning pipes 721 clean a portion including the outer wall which contacted a sample at the normal suction position P41. Also, the first cleaning liquid is supplied by the supply unit 73 via the tube 161 from the other end of the tube 161 into the sample dispensing probe 16. By the first cleaning liquid discharged from one end of the tube 161, the inner wall which contacted a sample in the sample dispensing probe 16 is cleaned.

In this manner, the cleaning unit 70 can clean the outer wall of the sample dispensing probe 16, which was contaminated by a sample when the sample dispensing probe 16 was stopped at the normal suction position P41, by discharging the first cleaning liquid from the first cleaning pipes 721. Also, the cleaning unit 70 can clean the inner wall of the sample dispensing probe 16 which was contaminated by a sample sucked at the normal suction position P41 by supplying the first cleaning liquid into the sample dispensing probe 16 from the other end and discharging that liquid from one end.

The second and third cleaning pipes 722 and 723 are disposed at positions lower than the first cleaning pipes 721. The second and third cleaning pipes 722 and 723 are arranged to clean the sample dispensing probe 16 under a special cleaning condition. Then, the second cleaning pipe 722 is arranged on a bottom portion in the cleaning tank main body 725 below the special cleaning upper stop position P2. Also, the third cleaning pipe 723 is arranged on the bottom portion of the cleaning tank main body 725 below the special cleaning upper stop position P3.

The second or third cleaning liquid supplied from the supply unit 73 flows in from the lower end of the second cleaning pipe 722. Then, the inflow second or third cleaning liquid flows upward and flows out from the upper end of the second cleaning pipe 722. Thus, the second cleaning pipe 722 is filled with the fresh second or third cleaning liquid. The first cleaning liquid supplied from the supply unit 73 flows in from the lower end of the third cleaning pipe 723. The inflow first cleaning liquid flows upward inside the third cleaning pipe 723 and flows out from the upper end of the third cleaning pipe 723. Thus, the third cleaning pipe 723 is filled with the fresh first cleaning liquid.

In this case, the driving mechanism 26 moves the sample dispensing probe 16, which sucked a sample at the special suction position P42 and discharged it into the reaction container 3, downward from the special cleaning upper stop position P2. Then, as shown in FIG. 8(*a*), the driving mechanism 26 stops the sample dispensing probe 16 having a portion including the outer wall which contacted a sample at the normal suction position P41 shown in FIG. 3(*a*) at a first dip position P21. The first dip position P21 is a special cleaning position where the sample dispensing probe 16 having the portion including the outer wall which contacted a sample at the normal suction position P41 is dipped into the second or third cleaning liquid in the second cleaning pipe 722. Thus, the cleaning unit 70 cleans the outer wall of the sample dispensing probe 16. Also, the cleaning unit 70 causes the sample dispensing probe 16 at the first dip position P21 to suck the second or third cleaning liquid by suction driving of the sample dispensing pump 16*a*. Thus, the cleaning unit 70 cleans the inner wall of the sample dispensing probe 16.

Next, the driving mechanism 26 moves the sample dispensing probe 16 which sucked the second or third cleaning liquid, and stops it at the normal cleaning position P1. Then, the cleaning unit 70 cleans the outer wall and inner wall, on which the second or third cleaning liquid is attached, of the sample dispensing probe 16 using the first cleaning liquid at the normal cleaning position P1.

In this manner, the cleaning unit 70 fills the second cleaning pipe 722 with the fresh second or third cleaning liquid, and stops the sample dispensing probe 16 at the first dip position P21. Then, the cleaning unit 70 can clean the outer wall of the sample dispensing probe 16, which was contaminated by a sample when the sample dispensing probe 16 was stopped at the normal suction position P41, using the second or third cleaning liquid. Also, the cleaning unit 70 causes the sample dispensing probe 16 to suck the second or third cleaning liquid. Then, the cleaning unit 70 can clean the inner wall of the sample dispensing probe 16, which was contaminated by a sample when the sample dispensing probe 16 sucked the sample, using the second or third cleaning liquid. Furthermore, the cleaning unit 70 supplies the first cleaning liquid to the sample dispensing probe 16 stopped at the normal cleaning position P1. Then, the cleaning unit 70 can wash away the second or third cleaning liquid attached to the sample dispensing probe 16.

Also, the driving mechanism 26 moves the sample dispensing probe 16, which sucked a sample at the special suction position P42 and discharged it into the reaction container 3, downward from the special cleaning upper stop position P2. Then, as shown in FIG. 8(b), the driving mechanism 26 stops the sample dispensing probe 16 having a portion including the outer wall which contacted a sample to be examined at the special suction position P42 shown in FIG. 3(b) at a second dip position P22. The second dip position P22 is a special cleaning position where a portion from one end (distal end) upward by a second distance D2 of the sample dispensing probe 16 having the portion including the outer wall which contacted a sample to be examined at the special suction position P42 is dipped into the second or third cleaning liquid in the second cleaning pipe 722. Thus, the cleaning unit 70 cleans the outer wall of the sample dispensing probe 16. Also, the cleaning unit 70 causes the sample dispensing probe 16 at the second dip position P22 to suck the second or third cleaning liquid by suction driving of the sample dispensing pump 16a. Thus, the cleaning unit 70 cleans the inner wall, which contacted a sample to be examined, of the sample dispensing probe 16.

In this manner, the cleaning unit 70 fills the second cleaning pipe 722 with the fresh second or third cleaning liquid, and stops the sample dispensing probe 16 at the second dip position P22. Then, the cleaning unit 70 can clean the outer wall of the sample dispensing probe 16, which was contaminated by a sample to be examined when the sample dispensing probe 16 was stopped at the special suction position P42, using the second or third cleaning liquid. Also, the cleaning unit 70 causes the sample dispensing probe 16 to suck the second or third cleaning liquid. Then, the cleaning unit 70 can clean the inner wall of the sample dispensing probe 16, which was contaminated by a sample when the sample dispensing probe 16 sucked the sample, using the second or third cleaning liquid.

Also, the driving mechanism 26 moves the sample dispensing probe 16, which sucked the second or third cleaning liquid at the second dip position P22, to a special inner wall cleaning position P13 located between the normal cleaning position P1 and, for example, the special cleaning upper stop position P3, and stops it at that position, as shown in FIG. 9. Then, the cleaning unit 70 supplies the first cleaning liquid from the supply unit 73 to the sample dispensing probe 16 at the special inner wall cleaning position P13. Thus, the cleaning unit 70 cleans the inner wall, on which the second or third cleaning liquid is attached, of the sample dispensing probe 16. The driving mechanism 26 stops the sample dispensing probe 16 after a sample to be examined sucked at the special suction position P42 was discharged into the reaction container 3, at the special inner wall cleaning position P13. Then, the cleaning unit 70 supplies the first cleaning liquid from the supply unit 73 to the sample dispensing probe 16. Thus, the cleaning unit 70 cleans the inner wall, which contacted the sample to be examined, of the sample dispensing probe 16.

In this way, the cleaning unit 70 supplies the first cleaning liquid to the sample dispensing probe 16 stopped at the special inner wall cleaning position P13. Then, the cleaning unit 70 can wash away the second or third cleaning liquid attached to the inner wall of the sample dispensing probe 16 when the sample dispensing probe 16 sucked the cleaning liquid at the second dip position P22. Also, the cleaning unit 70 can clean the inner wall of the sample dispensing probe 16, which was contaminated by a sample to be examined when the sample dispensing probe 16 sucked the sample at the special suction position P42.

The driving mechanism 26 moves the sample dispensing probe 16, the inner wall of which was cleaned using the first cleaning liquid at the special inner wall cleaning position P13, downward from the special cleaning upper stop position P3. Then, as shown in FIG. 10, the driving mechanism 26 stops the sample dispensing probe 16 including the outer wall which contacted the second or third cleaning liquid at the second dip position P22 or the sample dispensing probe 16 including the outer wall which contacted a sample to be examined at the special suction position P42 at a third cleaning position P31. The third cleaning position P31 is a cleaning position at which a portion from one end (distal end) of the sample dispensing probe 16 to an upward position by a third distance D3 is dipped in the first cleaning liquid in the third cleaning pipe 723. Thus, the cleaning unit 70 cleans the outer wall of the sample dispensing probe 16.

In this manner, the cleaning unit 70 fills the third cleaning pipe 723 with the fresh first cleaning liquid, and stops the sample dispensing probe 16 at the third cleaning position P31. Thus, the cleaning unit 70 can wash away the second or third cleaning liquid attached to the outer wall of the sample dispensing probe 16 when the sample dispensing probe 16 was stopped at the second dip position P22. Also, the cleaning unit 70 can clean the outer wall of the sample dispensing probe 16, which was contaminated by a sample to be examined when the sample dispensing probe 16 was stopped at the special suction position P42, using the first cleaning liquid.

The drain pipe 724 is arranged on the lower end portion of the cleaning tank main body 725, and drains the first cleaning liquid discharged from the first cleaning pipe 721, the second or third cleaning liquid flowing out from the second cleaning pipe 722, and the first cleaning liquid flowing out from the third cleaning pipe 723 to the outside of the cleaning tank main body 725.

The cleaning tank main body 725 holds the first to third cleaning pipes 721 to 723, and the drain pipe 724.

The cleaning tank main body 725 is arranged to guide, to the drain pipe 724, the first cleaning liquid discharged from the first cleaning pipe 721, the second or third cleaning liquid flowing out from the second cleaning pipe 722, and the first cleaning liquid flowing out from the third cleaning pipe 723 while preventing these liquids from leaking and scattering. Then, the cleaning tank main body 725 has two notches 725a which allow the sample dispensing probe 16 that moves between the sample position P4 and reaction position PS to pass through the cleaning tank 72.

The supply unit 73 shown in FIG. 5 includes a pump 731 required to suck the first cleaning liquid stored in the first tank 711 of the tank 71 and to supply it to the first or third cleaning pipe 721 or 723 of the cleaning tank 72, a pump 732 required to suck the first cleaning liquid in the first tank 711 and to supply it to the sample dispensing probe 16, and a pump 733 required to suck the second or third cleaning liquid stored in the second or third tank 712 or 713 and to supply it to the second cleaning pipe 722.

Also, the supply unit 73 includes a three-way electromagnetic valve 734 which is disposed between the pump 731 and cleaning tank 72, and is drive-controlled by the driving control unit 27 of the analysis control unit 25, a branch pipe 735 which is disposed between the three-way electromagnetic valve 734 and the cleaning tank 72, and branches the cleaning liquid from the three-way electromagnetic valve 734 to supply it to the two first cleaning pipes 721 of the cleaning tank 72, and a three-way electromagnetic valve 736 which is disposed between the second and third tanks 712 and 713 and the pump 733, and is drive-controlled by the driving control unit 27.

Then, in the outer wall cleaning operation of the sample dispensing probe 16 stopped at the normal cleaning position P1, the three-way electromagnetic valve 734 opens a path between the pump 731 and first cleaning pipes 721 and closes a path between the pump 731 and third cleaning pipe 723. Then, the pump 731 sucks the first cleaning liquid in the first tank 711. The pump 731 supplies the sucked first cleaning liquid to the first cleaning pipes 721. With this supply, the first cleaning pipes 721 discharge the first cleaning liquid. Also, in the inner wall cleaning operation of the sample dispensing probe 16, the pump 732 sucks the first cleaning liquid in the first tank 711. The pump 732 supplies the sucked first cleaning liquid to the sample dispensing probe 16. With this supply, the sample dispensing probe 16 discharges the first cleaning liquid.

In the outer wall cleaning operation of the sample dispensing probe 16 stopped at the first dip position P21 and second dip position P22, the three-way electromagnetic valve 736 opens a path between the pump 733 and second tank 712, and closes a path between the pump 733 and third tank 713. Then, the pump 733 sucks the second cleaning liquid in the second tank 712. The pump 733 supplies the sucked second cleaning liquid to the second cleaning pipe 722. With this supply, the second cleaning pipe 722 is filled with the second cleaning liquid. Also, in the inner wall cleaning operation of the sample dispensing probe 16, the sample dispensing pump 16a makes a suction operation to suck the second cleaning liquid in the second cleaning pipe 722 into the sample dispensing probe 16.

In the outer wall cleaning operation of the sample dispensing probe 16 stopped at the first dip position P21 and second dip position P22, the three-way electromagnetic valve 736 opens a path between the pump 733 and the third tank 713, and closes a path between the pump 733 and the second tank 712. Then, the pump 733 sucks the third cleaning liquid in the third tank 713. The pump 733 supplies the sucked third cleaning liquid to the second cleaning pipe 722. With this supply, the second cleaning pipe 722 is filled with the third cleaning liquid. Also, in the inner wall cleaning operation of the sample dispensing probe 16, the sample dispensing pump 16a makes a suction operation to suck the third cleaning liquid in the second cleaning pipe 722 into the sample dispensing probe 16.

In the inner wall cleaning operation of the sample dispensing probe 16 stopped at the special inner wall cleaning position P13, the pump 732 sucks the first cleaning liquid in the first tank 711. The pump 732 supplies the sucked first cleaning liquid to the sample dispensing probe 16. With this supply, the sample dispensing probe 16 discharges the first cleaning liquid.

In the outer wall cleaning operation of the sample dispensing probe 16 stopped at the third cleaning position P31, the three-way electromagnetic valve 734 opens a path between the pump 731 and the third cleaning pipe 723, and closes a path between the pump 731 and first cleaning pipes 721. Then, the pump 731 sucks the first cleaning liquid in the first tank 711. The pump 731 supplies the sucked first cleaning liquid to the third cleaning pipe 723. With this supply, the third cleaning pipe 723 is filled with the first cleaning liquid.

Note that the cleaning unit 70 may include a plurality of cleaning pipes corresponding to a plurality of cleaning liquids as one modification. For example, the cleaning unit 70 includes the plurality of first cleaning pipes 721 which discharge the first cleaning liquid, the second cleaning pipe 722 which stores a second cleaning liquid, the third cleaning pipe 723 which stores the first cleaning liquid, and a fourth cleaning pipe (not shown) which stores the third cleaning liquid. In this modification, in the sectional views of the cleaning tank 72 shown in FIGS. 6(b) and 9, the second cleaning pipe 722 stores the second cleaning liquid. In addition, in the sectional views of the cleaning tank 72 shown in FIGS. 6(b) and 9, the fourth cleaning pipe (not shown) is added.

The fourth cleaning pipe has, for example, the same structure as that of the second and third cleaning pipes 722 and 723. In this modification, in FIG. 5, the second cleaning liquid stored in the second tank 712 is supplied to the second cleaning pipe 722 via the pump 733. Also, the third cleaning liquid stored in the third tank 713 is supplied to the fourth cleaning pipe (not shown) via a pump (not shown). Furthermore, in this modification, the three-way electromagnetic valve 736 is not necessary.

An example of the cleaning operation of the sample dispensing probe 16 when a plurality of samples to be examined are dispensed will be described below with reference to FIGS. 1, 2, 3, 4, 5, 6, 7, 8, 9, 10, 11, and 12.

An analysis parameter setting screen is displayed on the display unit 42. The operation unit 50 makes inputs required to set examination items A1 to An analyzable by the automatic analysis apparatus 100. Then, the operation unit 50 inputs the special suction position P42 as the suction position for the examination item A2. The operation unit 50 inputs the normal suction position P41 as the suction positions for the examination items A1 and A3 to An. After analysis parameters of the examination items A1 to An are input, the display unit 42 displays a special cleaning condition setting screen.

FIG. 11 shows an example of the special cleaning condition setting screen displayed on the display unit 42. This special cleaning condition setting screen 43 includes a "cleaning position" field, a "cleaning liquid type" field, and a "time" field. The "cleaning position" field is used to set an examination item when the outer wall of the sample dispensing probe 16 is required to be cleaned at the second dip position P22 or third cleaning position P31. The "cleaning liquid type" field is used for examination items which are influenced when the detergency of the first cleaning liquid is insufficient. The time" field is used to set an examination item which requires a longer cleaning time (second time) than a cleaning time (first time) of a normal cleaning operation. Then, the operation unit 50 makes inputs required to set corresponding examination items in these fields.

In the "cleaning position" field, the special suction position P42 is set. More specifically, for example, the examination item A2 (glycohemoglobin or the like) which is required to be analyzed using the lower layer sample is set in the "cleaning position" field. With this setting, before the next dispensing operation after that for analysis of the examination item A2 is complete, the cleaning unit 70 cleans the outer wall of the sample dispensing probe 16 using the second or third cleaning liquid at the second dip position P22 or cleans the outer wall of the sample dispensing probe 16 using the first cleaning liquid at the third cleaning position P31.

In this manner, according to this automatic analysis apparatus 100, since the sample dispensing probe 16 stopped at the special suction position P42 is stopped at the second dip position P22 or third cleaning position P31, the outer wall portion, which cannot be cleaned at the position of the normal cleaning condition, of the sample dispensing probe 16 contaminated by a sample to be examined can be cleaned.

The "cleaning liquid type" field includes "second cleaning liquid" and "third cleaning liquid" fields. Then, in the "second cleaning liquid" field, for example, the examination item A1 (hepatitis C virus (HCV) or the like) is set. The examination item A1 is an examination item, which requires high-sensitive analysis by cleaning the sample dispensing probe 16 using the second cleaning liquid after the dispensing operation of the first sample is complete, and is readily influenced by components contained in the first sample, of examination items which are influenced by a sample to be examined to be dispensed first (first sample) via the sample dispensing probe 16 upon analysis of a sample to be examined which is dispensed second (second sample) when two samples to be examined are successively dispensed. With this setting, when the examination item A1 is set as the second sample, the cleaning unit 70 cleans the outer wall and inner wall of the sample dispensing probe 16 using the second cleaning liquid at the first or second dip position P21 or P22 before a dispensing operation of the second sample is started after that of the first sample is complete.

In this manner, according to this automatic analysis apparatus 100, since the sample dispensing probe 16 is stopped at the first or second dip position P21 or P22 before the dispensing operation of a sample to be examined set with the examination item A1 is started, the outer wall and inner wall of the sample dispensing probe 16 can be cleaned using the second cleaning liquid having a higher detergency than the normal cleaning condition using the first cleaning liquid.

In the "third cleaning liquid" field, for example, the examination item A6, which can reduce the influence of the first sample, is set. The examination item A6 is an examination item which requires the sample dispensing probe 16 to be cleaned by using the third cleaning liquid after completion of the dispensing operation of the first sample of examination items influenced by the first sample via the sample dispensing probe 16 upon analysis of the second sample when two samples to be examined are successively dispensed.

With this setting, when the examination item A6 is set as the second sample, the cleaning unit 70 cleans the outer wall and inner wall of the sample dispensing probe 16 using the third cleaning liquid at the first or second dip position P21 or P22 before the dispensing operation of the second sample is started after completion of the dispensing operation of the first sample.

In this way, according to this automatic analysis apparatus 100, since the sample dispensing probe 16 is stopped at the first or second dip position P21 or P22 before the dispensing operation of a sample to be examined set with the examination item A6 is started, the outer wall and inner wall of the sample dispensing probe 16 can be cleaned using the third cleaning liquid having a higher detergency than the normal cleaning condition using the first cleaning liquid.

In the "time" field, an examination item which requires the sample dispensing probe 16 to be cleaned by taking a longer time (special time (second time) T1) as a special cleaning condition than a time (normal time (first time) T0) of the normal cleaning condition. That is, this examination item is, for example, the examination item A1 in which the influence of the first sample can be reduced among examination items influenced by the first sample via the sample dispensing probe 16 upon analysis using the second sample when two samples to be examined are successively dispensed.

With this setting, when the examination item A1 is set for the second sample, the outer wall is cleaned since the sample dispensing probe 16 is stopped at a cleaning position of any of the first dip position P21, second dip position P22, and third cleaning position P31 until the special time T1 is elapsed before the dispensing operation of the second sample is started after completion of the dispensing operation of the first sample. Also, when the examination item A1 is not set for the second sample, the cleaning unit 70 cleans the outer wall since the sample dispensing probe 16 is stopped at a cleaning position of any of the first dip position P21, second dip position P22, and third cleaning position P31 until the normal time T0 is elapsed before the dispensing operation of the second sample is started after completion of the dispensing operation of the first sample.

In this manner, according to this automatic analysis apparatus 100, since the sample dispensing probe 16 is stopped at a cleaning position of any of the first dip position P21, second dip position P22, and third cleaning position P31 for the special time T1, the outer wall and inner wall of the sample dispensing probe 16 can be cleaned stronger than the cleaning operation when the sample dispensing probe 16 is stopped at any cleaning position for the normal time T0.

FIG. 12 shows an example of a plurality of samples to be examined, and examination items and cleaning conditions set for the respective samples to be examined. For these samples B1 to B5 to be examined, for example, the examination items A1 to A4 are set. Then, the examination items A1 and A2 are set for the sample B1 to be examined. The examination item A2 is set for the sample B2 to be examined. Also, the examination item A1 is set for the sample B3 to be examined. The examination items A1 and A2 are set for the sample B4 to be examined. Furthermore, the examination items A3 and A4 are set for the sample B5 to be examined. The dispensing operation is made in an order of the sample B1 to be examined, the sample B2 to be examined, the sample B3 to be examined, the sample B4 to be examined, and the sample B5 to be examined. The cleaning unit 70 cleans the sample dispensing probe 16 under cleaning conditions set in the respective fields of the special cleaning condition setting screen 43 in FIG. 11 every time the dispensing operation of each of the samples B1 to B5 to be examined is complete.

In this case, the sample B1 to be examined is dispensed first for analysis of the examination item A1. Next, the sample B1 to be examined is dispensed second for analysis of the examination item A2. After the dispensing operation of the sample B1 to be examined is complete, the sample B2 to be examined is dispensed third for analysis of the examination item A2. After the dispensing operation of the sample B2 to be examined is complete, the sample B3 to be examined is dispensed fourth for analysis of the examination item A1. After the dispensing operation of the sample B3 to be examined is complete, the sample B4 to be examined is dispensed fifth for analysis of the examination item A1. Next, the sample B4 to be examined is dispensed sixth for analysis of the examination item A2. After the dispensing operation of the sample B4 to be examined is complete, the sample B5 to be examined is dispensed seventh for analysis of the examination item A3. Then, the sample B5 to be examined is dispensed eighth for analysis of the examination item A4.

Then, the last dispensing operation of the sample B1 to be examined is made for analysis of the examination item A2 set in the "cleaning position" field. Items other than the examination items A1, A4, and A6 set in the "cleaning liquid type" and "time" fields are set for the sample B2 to be examined. Therefore, before the dispensing operation of the sample B2 to be examined is started after completion of the dispensing operation of the sample B1 to be examined, the sample dispensing probe 16 is stopped at the special inner wall cleaning position P13 to clean the inner wall using the first cleaning liquid. Next, the sample dispensing probe 16 is stopped at the third cleaning position P31 for the normal time T0 to clean the outer wall using the first cleaning liquid.

In this manner, according to this automatic analysis apparatus 100, since the sample dispensing probe 16 stopped at the special suction position P42 is stopped at the third cleaning position P31 for the normal time T0 based on information of the examination item A2 required to execute the cleaning operation under the special cleaning condition set on the special cleaning condition setting screen 43, the outer wall portion of the sample dispensing probe 16, which is contaminated by the sample B1 to be examined and cannot be cleaned under the normal cleaning condition, can be cleaned. Thus, this automatic analysis apparatus 100 can prevent the adverse influence due to contamination of the sample B1 to be examined on the sample B2 to be examined, and can prevent analysis data of the examination item A2 using the sample B2 to be examined from being deteriorated.

The last dispensing operation of the sample B2 to be examined is made for analysis of the examination item A2 set in the "cleaning position" field. The examination item A1 set in the "second cleaning liquid" and "time" fields is set for the sample B3 to be examined. Therefore, before the dispensing operation of the sample B3 to be examined is started after completion of the dispensing operation of the sample B2 to be examined, the sample dispensing probe 16 is stopped at the second dip position P22 for the special time T1 to clean the outer wall and inner wall using the second cleaning liquid. Then, the sample dispensing probe 16 is stopped at the special cleaning position P13 to clean the inner wall using the first cleaning liquid. Furthermore, the sample dispensing probe 16 is stopped at the third cleaning position P31 to clean the outer wall using the first cleaning liquid.

In this manner, according to this automatic analysis apparatus 100, since the sample dispensing probe 16 stopped at the special suction position P42 is stopped at the second dip position P22 based on information of the examination items A1 and A2 required to execute the cleaning operation under the special cleaning condition set on the special cleaning condition setting screen 43, the outer wall and inner wall of the sample dispensing probe 16 can be cleaned using the second cleaning liquid having a higher detergency than the normal cleaning condition under which the sample dispensing probe 16 is stopped for normal time T0 using the first cleaning liquid. Thus, this automatic analysis apparatus 100 can prevent the adverse influence caused by contamination from the sample B2 to be examined to the sample B3 to be examined, and can prevent analysis data of the examination item A1 using the sample B3 to be examined from being deteriorated.

The last dispensing operation of the sample B3 to be examined is made for items other than the examination item A2 set in the "cleaning position" field. The examination item A1 set in the "second cleaning liquid" and "time" fields is set for the sample B4 to be examined. Therefore, before the dispensing operation of the sample B4 to be examined is started after completion of the dispensing operation of the sample B3 to be examined, the sample dispensing probe 16 is stopped at the first dip position P21 for the special time T1 to clean the outer wall and inner wall using the second cleaning liquid. Then, the sample dispensing probe 16 is stopped at the normal cleaning position P1 to clean the outer wall and inner wall using the first cleaning liquid.

In this manner, according to this automatic analysis apparatus 100, since the sample dispensing probe 16 stopped at the normal suction position P41 is stopped at the first dip position P21 for the special time T1 based on information of the examination item A1 required to execute the cleaning operation under the special cleaning condition set on the special cleaning condition setting screen 43, the outer wall and inner wall of the sample dispensing probe 16 can be cleaned using the second cleaning liquid having a higher detergency than the normal cleaning condition under which the sample dispensing probe 16 is stopped for normal time T0 using the first cleaning liquid. Thus, this automatic analysis apparatus 100 can prevent the adverse influence caused by contamination of the sample B3 to be examined on the sample B4 to be examined, and can prevent analysis data of the examination items A1 and A2 using the sample B4 to be examined from being deteriorated.

The last dispensing operation of the sample B4 to be examined is made for analysis of the examination item A2 set in the "cleaning position" field. Items other than the examination items A1 and A6 set in the "cleaning liquid type" and "time" field are set for the sample B5 to be examined. Therefore, before the dispensing operation of the sample B5 to be examined is started after completion of the dispensing operation of the sample B4 to be examined, the sample dispensing probe 16 is stopped at the special inner wall cleaning position P13 to clean the inner wall using the first cleaning liquid. Then, the sample dispensing probe 16 is stopped at the third cleaning position P31 for the normal time T0 to clean the outer wall using the first cleaning liquid.

In this way, according to this automatic analysis apparatus 100, since the sample dispensing probe 16 stopped at the special suction position P42 is stopped at the third cleaning position P31 for the normal time T0 based on information of the examination item A2 required to execute the cleaning operation under the special cleaning condition set on the special cleaning condition setting screen 43, the outer wall portion of the sample dispensing probe 16, which is contaminated by the sample B4 to be examined and cannot be cleaned under the normal cleaning condition can be cleaned. Thus, the adverse influence due to contamination of the sample B4 to be examined on the sample B5 to be examined can be prevented, and analysis data of the examination items A3 and A4 using the sample B5 to be examined can be prevented from being deteriorated.

When the last dispensing operation of the sample B5 to be examined is made for analysis of items other than the examination item A2 set in the "cleaning position" field, the cleaning operation is executed under the normal cleaning condition after completion of the dispensing operation of the sample B5 to be examined. Then, the sample dispensing probe 16 is stopped at the normal cleaning position P1 for the normal time T0 to clean the outer wall and inner wall using the first cleaning liquid. In this manner, according to this automatic analysis apparatus 100, when the normal cleaning operation is executed, the sample dispensing probe 16 is stopped at the normal suction position P41 to which the sample dispensing probe 16 can be quickly moved to clean the outer wall and inner wall of the sample dispensing probe 16.

According to this embodiment described above, the sample dispensing probe 16 can be cleaned based on information of the examination items set on the special cleaning condition setting screen 43. Then, based on the examination item set in the "cleaning position" field, before the dispensing operation of the second sample is started after completion of the dispensing operation of the first sample set with that examination item, the sample dispensing probe 16 is stopped at the second dip position P22 or third cleaning position P31, thereby cleaning the outer wall portion of the sample dispensing probe 16, which is contaminated by the first sample and cannot be cleaned at the position of the normal cleaning condition.

Also, according to this embodiment, based on the examination item set in the "second cleaning liquid" field, before the dispensing operation of the second sample set with that examination item is started, the sample dispensing probe 16 is stopped at the first or second dip position P21 or P22, thereby cleaning the outer wall and inner wall of the sample dispensing probe 16 using the second cleaning liquid having a higher detergency than the normal cleaning condition using the first cleaning liquid.

Furthermore, according to this embodiment, based on the examination item set in the "third cleaning liquid" field, before the dispensing operation of the second sample set with that examination item is started, the sample dispensing probe 16 is stopped at the first or second dip position P21 or P22, thereby cleaning the outer wall and inner wall of the sample dispensing probe 16 using the third cleaning liquid having a higher detergency than the normal cleaning condition using the first cleaning liquid.

Moreover, according to this embodiment, based on the examination item set in the "time" field, before the dispensing operation of the second sample set with that examination item is started, the sample dispensing probe 16 is stopped at a cleaning position of any of the first dip position P21, second dip position P22, and third cleaning position P31 for the special time T1, thereby cleaning the outer wall and inner wall of the sample dispensing probe 16 stronger than the cleaning operation in which the sample dispensing probe 16 is stopped at any of the above cleaning positions for the normal time T0.

As described above, according to this automatic analysis apparatus 100, the adverse influence due to contamination of the first sample on the second sample can be prevented, and analysis data of the examination item using the second sample can be prevented from being deteriorated.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An apparatus comprising:
   a sample dispensing probe configured to perform a dispensing operation by sucking a sample of an examination item from a sample container, the sample of the examination item being sucked when the sample dispensing probe is at one of a first suction height and second suction height, and discharging the sample of the examination item into a reaction container;
   a cleaner comprising a first cleaning station, a second cleaning station on a first side of the first cleaning station, and a third cleaning station on a second side of the first cleaning station opposite the first side of the first cleaning station, the first cleaning station, the second cleaning station, and the third cleaning station being configured to clean the sample dispensing probe using a first cleaning liquid, a second cleaning liquid, and the first cleaning liquid respectively, the first cleaning station including a cleaning-liquid pipe with at least one outlet, the second cleaning station and the third cleaning station each including a respective cleaning-liquid pipe with a respective outlet, and the outlet of the second cleaning station and the outlet of the third cleaning station each being positioned lower than the outlet of the first cleaning station;
   a driving mechanism configured to move the sample dispensing probe along a moving path that includes the first cleaning station, the second cleaning station, and the third cleaning station, and to move the sample dispensing probe such that a lower end of the sample dispensing probe is moved to the first suction height and the second suction height, the second suction height being positioned lower than the first suction height; and
   a controller programmed to
      cause the driving mechanism to move the sample dispensing probe to the first cleaning station, after the sample of the examination item is sucked at the first suction height, and
      cause the driving mechanism to move the sample dispensing probe to at least one of the second cleaning station and the third cleaning station, after the sample of the examination item is sucked at the second suction height, and
      cause the driving mechanism to stop the sample dispensing probe at two different positions, upon the driving mechanism moving the sample dispensing probe to either the second cleaning station or the third cleaning station.

2. The apparatus according to claim 1, wherein, the first cleaning station further includes that the at least one outlet of the first cleaning station includes a plurality of outlets arranged to horizontally discharge the first cleaning liquid toward the sample dispensing probe, the plurality of outlets including a first outlet configured to emit a first stream in a first direction and a second outlet arranged diametrically opposed to the first outlet and configured to emit a second stream in a second direction opposite the first direction.

3. The apparatus according to claim 1, wherein the controller is further programed to cause the apparatus to
   suck, using the sample dispensing probe at the second suction height, the sample of the examination item,
   discharge the sample of the examination item into the reaction container, and
   then move, using the driving mechanism, the sample dispensing probe to at least one of the second cleaning station and the third cleaning station.

4. The apparatus according to claim 1, wherein the controller is further programed to cause the apparatus to
move, using the driving mechanism, the sample dispensing probe to the second cleaning station and cleaning the sample dispensing probe,
move, using the driving mechanism, the cleaned sample dispensing probe to the sample container,
suck, using the sample dispensing probe at the second suction height, the sample of the examination item, and
discharge the sample of the examination item into the reaction container.

5. The apparatus according to claim 2, wherein the controller is further programed to cause the apparatus to
suck, using the sample dispensing probe at the second suction height, the sample of the examination item,
discharge the sample of the examination item into the reaction container,
move, using the driving mechanism, the sample dispensing probe to the first cleaning station and remaining at the first cleaning station for a first time, and
then move, using the driving mechanism, the sample dispensing probe to one of the second cleaning station and the third cleaning station and remaining for a second time, wherein
the second time is greater than the first time.

6. The apparatus according to claim 1, further comprising a detector configured to detect a height of the examination item contained in the sample container,
wherein the first suction height is a first distance below the height of the examination item in the sample container, and
the second suction height is a second distance below the height of the examination item in the sample container.

7. The apparatus according to claim 1, wherein
the cleaning-liquid pipe of the first cleaning station is configured to discharge the first cleaning liquid toward the sample dispensing probe, when the sample dispensing probe is at the first cleaning station,
the cleaning-liquid pipe of the second cleaning station is configured to provide the second cleaning liquid to clean the sample dispensing probe, when the sample dispensing probe is at the second cleaning station, and
the cleaning-liquid pipe of the third cleaning station is configured to provide the first cleaning liquid to clean the sample dispensing probe, when the sample dispensing probe is at the third cleaning station.

8. The apparatus according to claim 1, wherein
the cleaner is further configured to clean the sample dispensing probe at the second cleaning station using a third cleaning liquid.

9. The apparatus according to claim 6, wherein, at the second cleaning station,
the driving mechanism is further configured to immerse the end of the sample dispensing probe in the second cleaning liquid to a depth of a first dip position or a second dip position the first dip position is a distance not less than the first distance and less than the second distance, and
a second dip position is a distance greater than the second distance.

10. An automatic analysis apparatus, comprising:
a sample dispensing probe configured to perform a dispensing operation by sucking a sample of an examination item from a sample container at one of a first suction height and second suction height, and discharging the sample into a reaction container;
an analyzer configured to receive photometry data representing the sample in the reaction container and to perform analysis on the photometry data;
a cleaner comprising a first cleaning station, a second cleaning station on a first side of the first cleaning station, and a third cleaning station on a second side of the first cleaning station opposite the first side of the first cleaning station, the first cleaning station, the second cleaning station, and the third cleaning station being configured to clean the sample dispensing probe using a first cleaning liquid, a second cleaning liquid, and the first cleaning liquid respectively, the first cleaning station, the second cleaning station, and the third cleaning station each including a respective cleaning-liquid pipe with a respective outlet, and the outlet of the second cleaning station and the outlet of the third cleaning station each being positioned lower than the outlet of the first cleaning station;
a driving mechanism configured to move the sample dispensing probe along a moving path that includes the first cleaning station, the second cleaning station, and the third cleaning station, and to move the sample dispensing probe such that a lower end of the sample dispensing probe is moved to the first suction height and the second suction height, the second suction height being positioned lower than the first suction height; and
a controller programmed to
cause the driving mechanism to move the sample dispensing probe to the first cleaning station, after the sample of the examination item is sucked at the first suction height, and
cause the driving mechanism to move the sample dispensing probe to at least one of the second cleaning station and the third cleaning station, after the sample of the examination item is sucked at the second suction height, and
cause the driving mechanism to stop the sample dispensing probe at two different positions, upon the driving mechanism moving the sample dispensing probe to either the second cleaning station or the third cleaning station.

* * * * *